United States Patent [19]
Leahey et al.

[11] Patent Number: 5,331,163
[45] Date of Patent: * Jul. 19, 1994

[54] RADIOACTIVE AREAL DENSITY DETECTOR WITH SCINTILLATING RECEIVER

[75] Inventors: Harry S. Leahey; W. Robert Binns; John W. Epstein; Joseph Klarmann, all of St. Louis, Mo.

[73] Assignee: Washington University, St. Louis, Mo.

[*] Notice: The portion of the term of this patent subsequent to Jun. 2, 2009 has been disclaimed.

[21] Appl. No.: 839,907

[22] Filed: Feb. 21, 1992

Related U.S. Application Data

[63] Continuation-in-part of Ser. No. 659,904, Feb. 25, 1991, Pat. No. 5,118,940.

[51] Int. Cl.$^5$ .................... G01N 23/16; G01N 23/06
[52] U.S. Cl. .................................. 250/367; 378/54; 250/308
[58] Field of Search ............. 250/308, 307, 306, 367, 250/442.11; 378/50, 54, 57

[56] References Cited

U.S. PATENT DOCUMENTS

| | | | |
|---|---|---|---|
| 3,868,510 | 2/1975 | Murata et al. | 250/308 |
| 4,682,034 | 7/1987 | Saint et al. | |
| 4,696,023 | 9/1987 | Kuusi | 378/46 |

FOREIGN PATENT DOCUMENTS 0187202  8/1987  Japan ................... 250/306

Primary Examiner—Paul M. Dzierzynski
Assistant Examiner—Richard Hanig
Attorney, Agent, or Firm—Rogers, Howell & Haferkamp

[57] ABSTRACT

Apparatus for continuously determining the areal density along a length of a material includes a radioactive source and a scintillating receiver. In a first embodiment, the invention measures the thickness of a traveling web simultaneously at multiple points across its full width. The apparatus includes a radioactive source which extends across one side of the web. A detector array, on the opposite side of the web, detects the emission from the source through the web. The array includes scintillating fibers and multi- or single-anode photomultipliers which may be connected by a scintillating or non-scintillating fiber optic elements to the photomultiplier. In a second embodiment, the invention continuously detects the fill level of a plurality of containers as they are conveyed between the receiver and detector. A scintillating fiber receiver may have its fibers arranged either vertically or horizontally. When arranged horizontally, the fibers may be grouped and conduct photons to single anodes of a multi-anode photomultiplier tube to provide direct physical measurement of the fill level. Still another receiver includes a plastic scintillator sheet directly coupled to a photomultiplier tube.

30 Claims, 6 Drawing Sheets

RADIOACTIVE AREAL DENSITY DETECTOR WITH SCINTILLATING RECEIVER

CROSS-REFERENCE TO RELATED APPLICATION

This application is a continuation-in-part of application Ser. No. 07/659,904 filed Feb. 25, 1991, now U.S. Pat. No. 5,118,940.

BACKGROUND AND SUMMARY OF THE INVENTION

This invention relates to the continuous measurement of the areal density of a material or object. Any material which tends to attenuate a radioactive source as the material is moved between a radioactive source and a receiver in direct proportion to its areal density, i.e. the density of the material times its thickness. The present invention includes a scintillator for sensing the attenuated radiation which traverses the material and generates light which may be transmitted by a light pipe to an anode of a photomultiplier device for further amplification and processing. The receiver has several embodiments which uniquely utilize scintillating materials and, in some cases, combining them with light pipes for continuous measurement of the areal density of the material throughout a substantial length or width thereof. One receiver embodiment includes a plurality of scintillating optical fibers which may be arranged contiguously and transversely to the radiation source such that light generated by the scintillator embedded in the fiber is piped directly through the fiber to a photomultiplier device for collection and amplification. If a multi-anode photomultiplier device is utilized, the areal density of the material at specific locations thereof may be conveniently collected on a continuous basis. When position data is not desired, a scintillator may be directly coupled to the photomultiplier device. In still other embodiments, a scintillator film may be utilized with optical fibers as light pipes only for transmitting the photons from the scintillator film to the photomultiplier device.

The subject invention may be utilized in several different formats and applications, depending upon the desires of the user. Several of these are disclosed and described herein with specific features adapted for implementing the invention to the specific task at hand. However, the scope of the invention should be considered to be broader than the scope of the particular examples and applications disclosed herein which are intended to be merely exemplary thereof.

One specific application of this invention relates to the continuous measurement of the areal density of a traveling web, and in particular, to the determination of the areal density thereof simultaneously at multiple points which substantially cover the entire width thereof. The preferred embodiment discloses an application of this invention to the problem of determining the basis weight of a paper web, however, the invention may be used to determine the areal density Of many different kinds of materials, such as metal, woven materials such as cotton and synthetic textiles, and non-woven materials such as plastics, etc. Thusly, although the term web is used throughout, it should be understood that it refers to any of these materials.

Presently, the basis weight of a web of paper is determined using a single source which emits Beta or Gamma radiation particles. The radiation passes through the paper web and is measured by a detector on the other side of the web of paper. As it passes through the web, the beam of radiation is attenuated. The attenuation is proportional to the density and thickness of the web, as expressed in terms of its areal density. Thus, the signal received is proportional to the basis weight of the paper web.

The source that is used is generally quite small, only an inch or two in diameter. Consequently, the detector must be mobile to measure the full width of the paper web. Presently, the detector is mounted on an endless belt and travels to and fro across the width of the paper. Thus, at any one time, the information received is only determinative of the areal density of the paper at a single point. To determine the basis weight of the paper, thousands of measurements have to be taken as the device scans across the paper. Because the paper is moving past the measuring device quickly, i.e. up to 7,000 FPM for newsprint, the time spent by the device in measuring a specific part of the web, in the cross direction, is limited. Further, because only an average basis weight, over many thousands of feet of paper, can be determined, it is not possible to use the present scanners to investigate short time span variables which affect basis weight and therefore affect product quality.

Another example of a prior art device is shown in U.S. Pat. No. 3,868,510 entitled Method for Sensing Profile of Sheet or Plate Materials. This device discloses a radiation thickness detector which utilizes a radiation source which is physically moved transversely to a moving sheet of steel. The detector comprises a flat detector plate made from a scintillator with a number of light pipes secured to the scintillator for routing light generated therein to a single anode photomultiplier such as a photoelectron multiplication tube. This device, as with the other prior art device disclosed herein, measures the relative thickness of the moving web at only one point, that point being where the source is positioned. Therefore, this device provides a position sensitive measurement of the thickness of the web also.

In accordance with the invention, one of the preferred embodiments discloses a paper basis weight detector for simultaneously determining the basis weight of a web of paper at multiple points across the width thereof. The detector includes a stationary radioactive source which emits radiation which passes through the paper web. A stationary receiver detects the radiation which passes through the web and converts the radiation to light of a known wavelength. A multi-anode photomultiplier tube (or array of photomultiplier tubes) optically connected to the receiver collects the light which is generated by the receiver. The output of the photomultiplier tube is directed to an analyzer which counts the light photons generated and thereby determines the basis weight of said paper webs.

The receiver includes a plurality of scintillating optical fibers formed into an array. The fibers preferably extend transversely to the direction of motion of said paper web. The array is approximately 2-3 cm in width and 15 cm in length. The array, however, may be of an endless variety of dimensions. The receiver preferably includes a plurality of such arrays which, together, extend the width of the paper.

The fibers of the array extend from the detection region to the photomultiplier tube. The scintillating fibers from each array may be joined into a single non-scintillating fiber optic element which is connected to the photomultiplier tube. Preferably, each array of fiber optics is connected to a different anode to allow for discrete measurement at multiple points across the width of the paper web.

The receiver may alternately comprise a scintillator and non-scintillating optical fibers connected thereto. The scintillator may include a scintillating or phosphor screen to which the fibers are connected in an array. Alternatively, the scintillator may include a plurality of discrete scintillating elements, there being one such element at an end of each said fiber. Preferably, each array of fiber optics is connected to a separate anode of the photomultiplier tube to allow simultaneous measurement at multiple points across the paper web.

The detector preferably can detect a wide range of radiation particles, and in an experimental prototype can detect, e.g., approximately $5.5 \times 10^6$ Beta and related radiation particles/second. To accomplish this, the source preferably includes a source of Strontium-90, Cesium-137, or other similar radioactive or X-ray emitting source. The source strength used depends upon the specific measurement intended. The Beta particles or X-rays emitted by the source may, optionally, be passed through a collimator.

Still another specific application of the subject invention relates to the continuous measurement of the fill level of a beverage can as a plurality of beverage cans are conveyed therepast. In this application, a linear radioactive source is positioned directly opposite a receiver, and both are spaced apart to provide a path for the plurality of containers as they are conveyed therethrough. A typical example for this specific application would include the detection of a fill level of beer or soft drink in an aluminum can. The receiver may be comprised of an array of scintillating fibers, with the array being oriented either vertically or horizontally. Also, the array may be positioned along the entire height of the container, or may instead be arranged to cover only that upper portion of the container which might be expected to be partially empty. Additionally, the horizontal array of fibers may be grouped and separately coupled to individual anodes of a multi-anode photomultiplier tube, or other photomultiplier device, such that a more accurate indication of the actual fill level may be detected. Alternately, either the vertical or horizontal array of scintillating fibers may be connected to a single anode photomultiplier tube and the relative strength of the signal would be representative of the level of fill in the particular container being sensed. In this particular embodiment of the receiver, scintillating fibers may be used, or, as suggested in other embodiments of other examples herein, a scintillator sheet with optical fiber may be used, or portions of scintillating fiber integrally joined to optical fiber. In still a third embodiment of this specific application, the receiver may be comprised of a plastic scintillator sheet which is directly coupled to a single anode photomultiplier tube, thereby eliminating the use of any optical fibers, scintillating or non-scintillating. In this embodiment, the relative strength of the signal would be an indicator of the fill level of fluid in the container.

One of the objects of the present invention is to provide a radioactive areal density detector with a receiver having a scintillator for converting radiation which traverses an object or material whose areal density is to be detected into a light signal representative thereof. A photomultiplier device may be conveniently coupled to the scintillator and amplifies the light signal for further use. The scintillator may be comprised of either scintillating fibers, or a scintillator material. Optical fibers, if used, conveniently light pipe the photons generated by the scintillator to the photomultiplier device. A single or multi-anode photomultiplier device can provide either one signal, or multiple signals, representative of areal densities at different physical locations throughout the material or device being sensed. The scintillating fibers may be arranged, horizontally, vertically, or in other arrangements as suits the particular application. Specific embodiments representing applications of the present invention in solving particular problems incorporate additional inventive features.

Another object of the present invention is to provide an apparatus which can simultaneously and continuously, in addition to very quickly, determine the thickness of a traveling web at multiple points across the width thereof. Such cannot currently be done with moving scanners.

Another object is to provide such an apparatus which will provide basis weight measurements of a paper web at much shorter time intervals than presently possible.

Another object is to provide such an apparatus which can be situated either at the web end or the dry end of a web of paper.

Another object is to provide such an apparatus which will produce an accurate weight profile of the full width and length of the web.

Another object of the present invention is to provide an apparatus which can continuously, in addition to very quickly, determine the fill level of a fluid in a container. The apparatus may include a linear radioactive source and a receiver mounted in spaced apart relationship such that the plurality of containers may be conveniently conveyed therebetween.

Another object of the present invention is to provide such an apparatus with a receiver incorporating scintillating fibers arranged in an array which is either vertically or horizontally situated with respect to the containers.

Another object of the invention is to provide such an apparatus which may detect the fill level in the container based on the relative strength of the radiation which traverses the container.

Another object of the invention is to provide such an apparatus which will provide a direct physical measurement of the fill level of fluid in a container by utilizing groups of scintillating fibers arranged horizontally with the output of each group being separately collected and amplified to provide separate signals.

These and other objects will become apparent to those skilled in the art in light of the following disclosure and accompanying drawings.

DESCRIPTION OF THE PREFERRED EMBODIMENT

Figure 1:
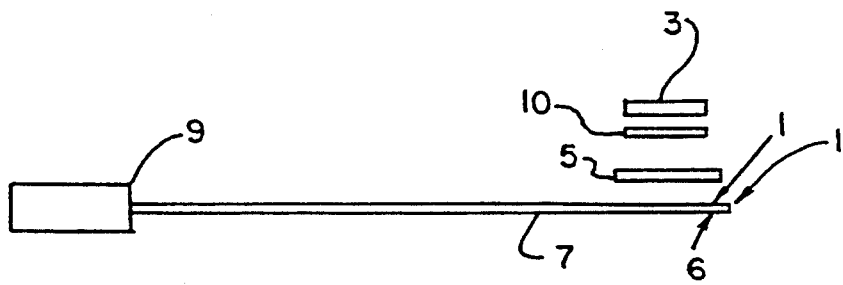
FIG. 1 is a schematic drawing showing one illustrative embodiment on the basis weight detector of the present invention.

Referring to FIG. 1, reference numeral 1 indicates a basis weight detector of the present invention. Detector 1 includes a stationary radioactive source 3 positioned on one side of a moving web 5 of paper. The source 3 extends transversely to the direction of movement of the web. The source is preferably Strontium 90 (Sr-90). Other Beta or X-ray emitting sources, such as Cesium, or the like, may be used. The source may comprise a plurality of Sr-90 sources placed at intervals across the width of the paper web, or a unitary Sr-90 source extending the width of the paper web. Other energy emitting sources may also be used, such as ultraviolet light, depending on the material whose thickness is being sensed.

The source 3 emits radiation particles which pass through the paper web 5. The radiation particles include such particles as Beta or Gamma particles. The beam of radiation particles is picked up by a detector array 6 comprising a scintillating element positioned on a side of the paper web opposite the source 3. The array 6 extends some width, e.g., approximately 15 cm, of the paper web 5 and is connected to a photomultiplier tube (PMT) 9, such as multi-anode PMT or a Quantacon PMT available from Hamamatsu Co., Hamamatsu, Japan, or other common PMT's, by the fiber optic elements 7.

When the radiation particles penetrate into the scintillator core of the scintillating fibers, they impart energy to the scintillator, causing the scintillator to emit photons of light. The fiber optic elements 7, of detector array 6, light pipe the photons and transfer them therethrough to multi-anode photomultiplier 9. The output of the photomultiplier is fed to a Pulse Height Analyzer (not shown) which counts the number of photons entering the photomultiplier. From this number, the basis weight or thickness of the paper can be determined.

The fibers 7 are preferably oriented transverse to the direction of motion of the paper web 5 to provide an average thickness at one cross-sectional area of the web 5. If desired, the fibers could be oriented along the direction of motion of web 5. This, however, would provide a basis weight along a longitudinal, rather than a transverse, cross-section of web 5. As is further described below, several detector arrays 6 may be used to extend across the full width of a web of paper.

The multi-anode tube of photomultiplier 9 may have as many as one hundred or more discrete anodes. Fibers 7 from each array 6 are connected to a different anode of photomultiplier 9. Thus, each group of fibers corresponds to a different location in the array. This allows for measurements at up to one hundred or more different areas across the width of the web which can be taken simultaneously. With these points spread across the width of paper web 5, basis weight calculations can be made continuously across the entire width of web 5. Further, if made fast enough, the calculations could provide nearly instantaneous basis weight determinations across the width of web 5.

To accurately determine basis weight of the paper, the detector 1 should have the sensitivity to measure small variations in thickness. The basic instrument sensitivity is governed by counting statistics and by the energy spectrum of the radiation emitted by source 3. For greater sensitivity in obtaining low energy electrons, a plate 10 is positioned between the source and the fiber. Plate 10 may be aluminum or another desired metal. Plate 10 allows for tuning the electron energy to the desired thickness measurement range. The thickness of plate 10 depends on the thickness of paper web 5 and the activity of sources 3.

EXAMPLE 1

The detector 1 was tested with KL type paper having nominal basis weights of 26, 56, 69, and 90 to determine the number of counts necessary to accurately determine the thickness or basis weight of the paper. The source 3 was uncollimated an 0.3 $\mu$Ci Sr-90 source, aluminum plate 10 was 0.020" thick, and fibers 7 were scintillating fibers 1.75 mm thick. The Sr-90 source energy emission was deposited on a circle about 1 cm in diameter which projected down onto the fibers.

Figure 2:
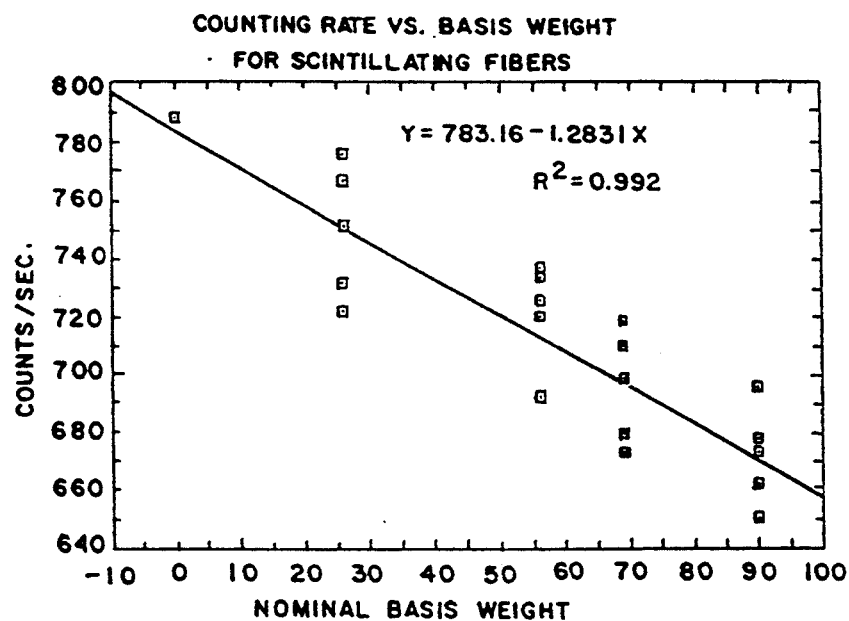
FIG. 2 is a graph comparing the count rate for an 0.3 $\mu$Ci Sr-90 source against various basis weights paper.

The area of paper samples was a rectangle with dimensions 1 cm×0.175 cm. The measurement represented an average over this small area. Since paper is non-uniform on this small scale, five samples of each of the different basis weight papers were used. In addition one run was taken for no paper in the gap (i.e. only aluminum plate 10 was between source 3 and the array 6). The counts were measured for a period of about 100 seconds. FIG. 2 shows the counting rates obtained for these paper samples and the blank. It shows that, although there is considerable scatter in the data for the different samples, as the basis weight of the paper increases, the number of counts decreases. The mean counting rate, plotted across the data points, has a rate of change 1.28 counts/sec/unit basis weight. Thus, for a unit change in basis weight, there will be a mean rate change of 1.28 parts out of about 750 counts/sec for twenty-six basis weight paper.

The number of decays (photons or electrons) that would have to be detected to determine a change in basis weight of 2% at three standard deviations of, for example, twenty-six basis weight paper; i.e. $0.02 \times 26 = 0.52$ basis weight units will now be calculated. The expected counting rate change would then be $0.52 \times 1.28$ counts/sec $= 0.67$ counts/sec out of a total rate of about 755 counts/sec. Therefore, the detector would have to be able to distinguish a fractional rate change of $0.67/755 = 8.8 \times 10^{-4}$. For one standard deviation ($\sigma$), the number of counts, N, required is determined from the following formula:

$$N = 1/\sigma^2 = 1/(8.8 \times 10^{-4})^2 = 1.3 \times 10^6$$

For three standard deviations it is three times as much. Since the ratio between two measurements is being taken, the number of counts (3N or $3.9 \times 10^6$) must be multiplied by the square root of two. Thus, $5.5 \times 10^6$ counts/second must be detected for this configuration.

EXAMPLE 2

Figure 3:
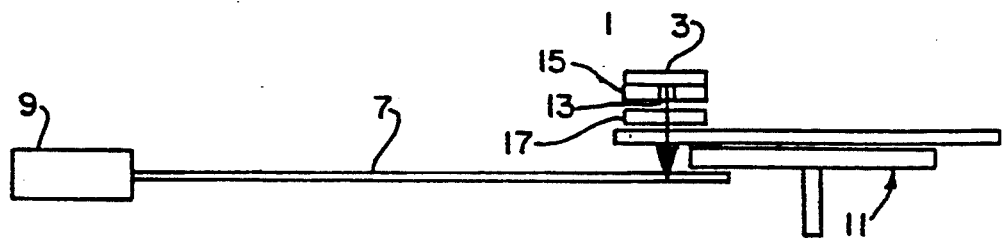
FIG. 3 is a schematic of a related testing apparatus used in determining the necessary count rate for an appropriately sensitive basis weight detector.

In this example, samples of paper 10 cm in diameter were tested on an apparatus as shown in FIG. 3. Six disks of KL-50 paper, and one disk each of KL-45, 47, and 54 paper were used. A paper sample was mounted on a turntable 11 for rotation of a rate of 7 sec/revolution. The source 3, an 0.5 mCi Sr-90 source, was placed above the paper. The source was collimated with a 1.6 mm hole 13 in a collimator 15. A 0.016" aluminum plate 17 was placed between the source and the paper. As the paper rotated, an annulus of about 1.6 mm in width and 8 cm in radius was swept out by the source on the paper. The electrons emitted by source 3 impinged on a one meter long scintillating fiber 7 which was connected to the Quantacon PMT 9. Measurements were taken for about 300 seconds.

Figure 4:
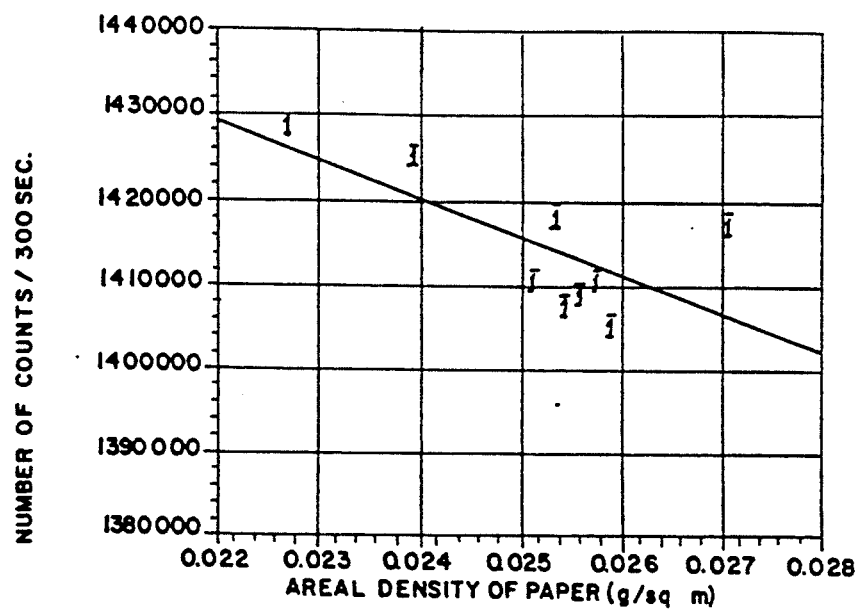
FIG. 4 is a graph comparing the count rate against the areal density of paper samples.

FIG. 4 shows the number of counts plotted vs. the areal density of the paper samples. Because the line fitted to the data points was outside of the error bars, FIG. 4 indicates that a systematic effect is present which has a greater effect than that of statistics.

Figure 5:
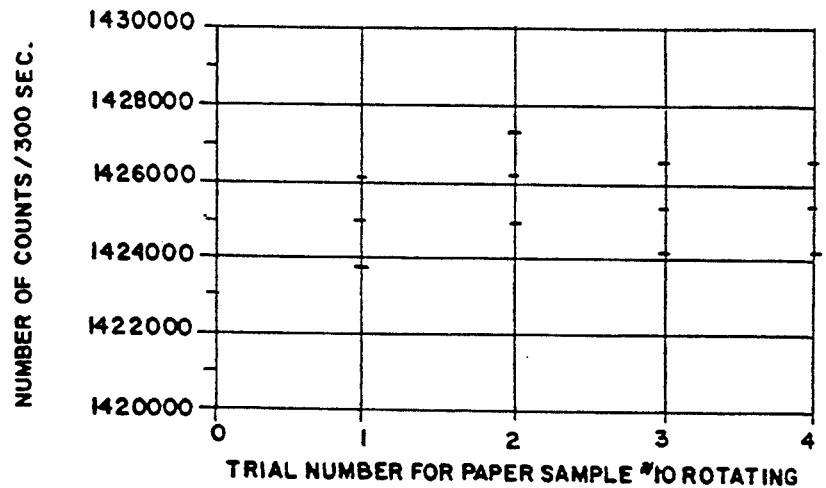
FIG. 5 is a graph comparing the count rate for a single paper sample.

Four data runs were taken for a single sample of paper with the paper rotating. The results, plotted in FIG. 5, show that the data points are within error bounds and thus agree, within statistics. Comparing FIG. 4 with FIG. 5 indicates that the fluctuations present in FIG. 4 are due to thickness non-uniformity, rather than to the instrument.

Figure 6:
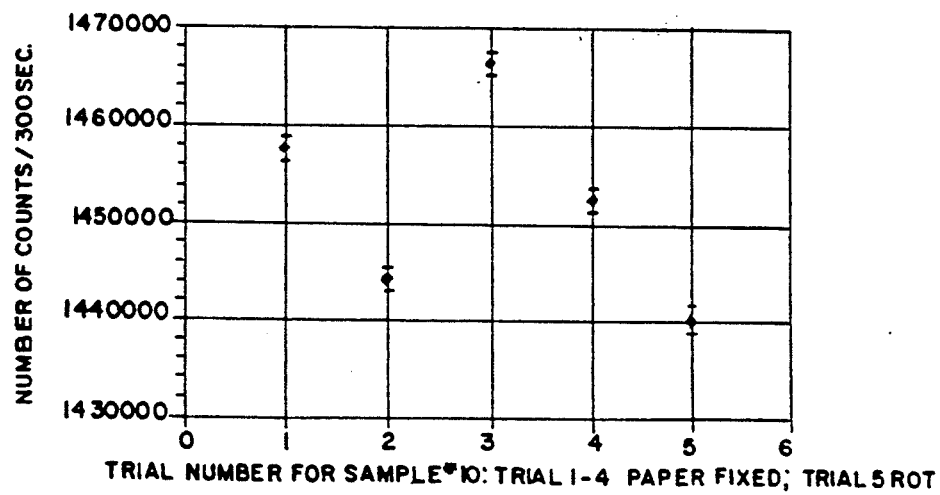
FIG. 6 is a graph comparing the count rate against a single non-rotating paper sample (trials 1–4), and the same sample rotating is plotted as trial 5.

Measurements were then taken with the sample of paper fixed in four different positions. The results are plotted in FIG. 6. In the fifth trial, the paper was rotating, and was thus not fixed, as were the other trials. FIG. 6 confirms that the scatter in the data points is due to real variations in paper thickness.

EXAMPLE 3

The device of FIG. 3 was then tested with Mylar sheets having known thicknesses to determine if the measuring device would give measurements which are consistent, within statistics. Eight sheets of Mylar 0.001" thick were stacked on top of one another followed by 0.0005" thick sheets. The samples were measured for a period of 300 seconds. The results, plotted in FIG. 7, fit within a straight line having a slope of $-2.458$ counts/sec/(g/M$^2$).

Figure 7:
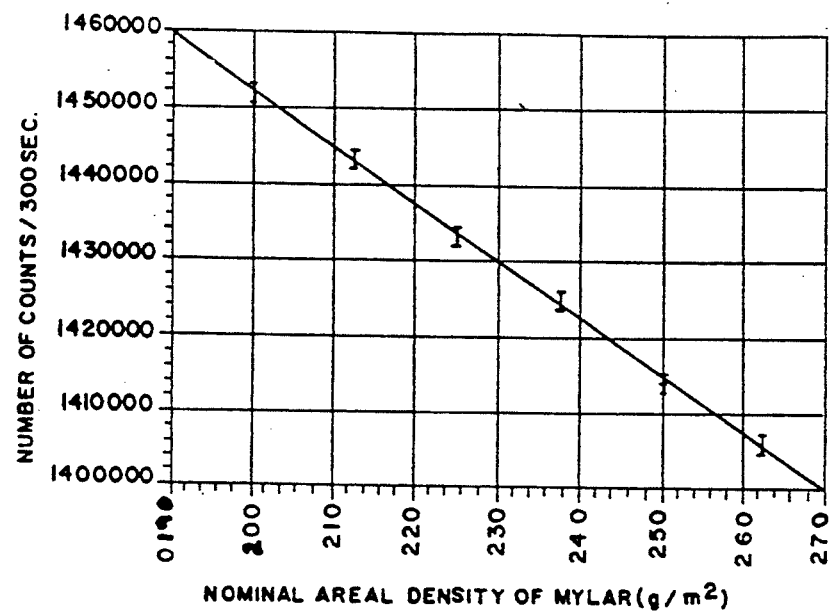
FIG. 7 is a graph comparing the count rate against samples having known thicknesses.

To measure the paper thickness to a precision of 2%, for example, of paper having an areal density of 240 g/m$^2$, the detector must be able to measure to a thickness of $0.02 \times 240 = 4.8$ g/m$^2$. The count rate that must be measured is the product of the slope and 4.8 g/m$^2$ which is 11.8 counts/sec. This is out of a total count rate of about $4.7 \times 10^3$ counts/sec (the count rate in FIG. 7 is about $1.4 \times 10^6$ counts in 300 sec). Thus, the detector must be able to distinguish a fractional rate change of $11.8/4,700 = 2.5 \times 10^{-3}$. To do this then requires $N = 1/\sigma^2 = 1.6 \times 10^5$ counts per second. For a $3\sigma$ level, this becomes $4.8 \times 10^5$ counts per second.

In this example, $4.7 \times 10^3$ counts/second was detected using a 1 cm length of a 1.75 mm wide fiber and a 0.3 $\mu$Ci source. The number of counts can be increased by using, for example, a 2 cm wide ribbon, rather than a 0.175 cm ribbon. This would increase the counting rate by a factor of about 11 bringing the number of counts/second to $5.4 \times 10^4$. To increase the number of counts to a count rate of $5.5 \times 10^6$ the activity of the Sr-90 source would have to be increased by a factor of 100, to 30 $\mu$Ci.

Figure 8:
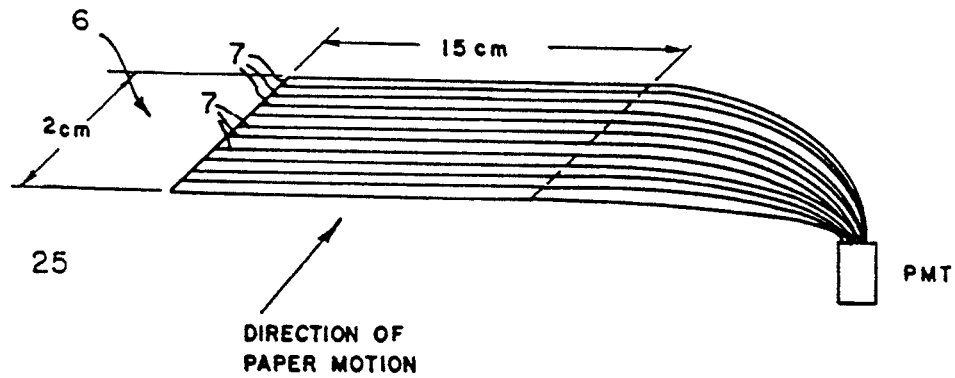
FIG. 8 is a schematic of a detector array for use in the basis weight detector.

The detector array 6 preferably consists of not one scintillating fiber as was used in the testing device of FIG. 3, but of many scintillating fibers 7 which may be made into a ribbon 25 having an active area of about $2 \times 15$ cm (FIG. 8). For purposes of this invention, the array of fibers need not be made into a ribbon to be usable.

The active area of about $2 \times 15$ cm is appropriate for this particular paper web application. It will be understood, however, that many other dimensions could be used. The fibers may be contiguous to form a continuous width ribbon, or they may be spaced to form a ribbon of discrete fibers.

If the detector has a fiber ribbon with width of 2 cm, and the electrons from a point radioactive source uniformly illuminate a 2 cm diameter circle on the fibers, then the geometry factor of the 2 cm circle would be increased by a factor of $\pi \times 1$ cm$^2$/0.175 = 18, giving a count rate of $3.8 \times 10^4$ counts/sec. Since up to $4.8 \times 10^5$ counts for a $3\sigma$ measurement may be needed, this would require 13 seconds using an 0.3 $\mu$Ci source, or 1 second if the source strength is increased to 4 $\mu$Ci.

The source is preferably distributed linearly along the length of array 6 to average the measurement over the 15 cm length of the fibers of the array. Forty of these sources 3 and ribbons 25 spaced approximately six inches apart would be needed to cover a twenty foot wide paper web. The forty sources give a total source activity of 0.16 mCi. This can be conveniently shielded to provide for safety.

The Sr-90 source is positioned so that the Beta decay electrons are emitted generally transverse to the optic axis of the fibers. Fibers 7 extend across the paper web transverse to the direction of motion of the paper web. Ribbon 25 is connected to a photomultiplier 9 by a non-scintillating optical fiber 27 using optical epoxy. Energy is pulsed through fiber 27 at three billionths of a second. See FIG. 9. But, in FIG. 8 the scintillating fibers that form the array connect directly to the photomultiplier tube.

The photons emitted by the scintillating fibers are emitted isotopically, with about 5% light piped in either direction along the fiber. Because of the loss of photons as they travel along the optical fibers and the typical quantum efficiencies of photomultiplier tubes (about 25%), only a few of the photons will be detected per Beta decay electron entering the fibers. For example, if the Beta particles penetrating through the paper deposit 100 KeV in the fibers, since it takes about 140 KeV to make a single blue photon in plastic scintillator with a polystyrene base, about 715 photons would be produced. As 5% are light piped in either direction, about thirty-six photons are light piped in either direction. If these are light piped over a distance of about two meters, the light intensity would be reduced by a factor of three, giving about twelve photons incident upon the photomultiplier tube photocathode. Taking into account the efficiency of photomultiplier tubes, about three photoelectrons per Beta decay electron result at the photomultiplier tube photocathode.

In FIG. 8, only one end of the fibers 7 is connected to the photomultiplier tube 9. The number of photoelectrons can be doubled by connecting either end of the fibers to the same photomultiplier tube. Because only a few photoelectrons are produced at the photocathode on the photomultiplier tube, a photomultiplier tube having a high gain is required.

The part of the fibers not in the active area (i.e. the fibers which do not receive any Beta particles) can be, but need not be, scintillating fibers. In fact, there will be improved light transmission if these fibers are non-scintillating fibers which are coupled to the scintillating fibers, as shown in FIG. 8.

Figures 9, 10:
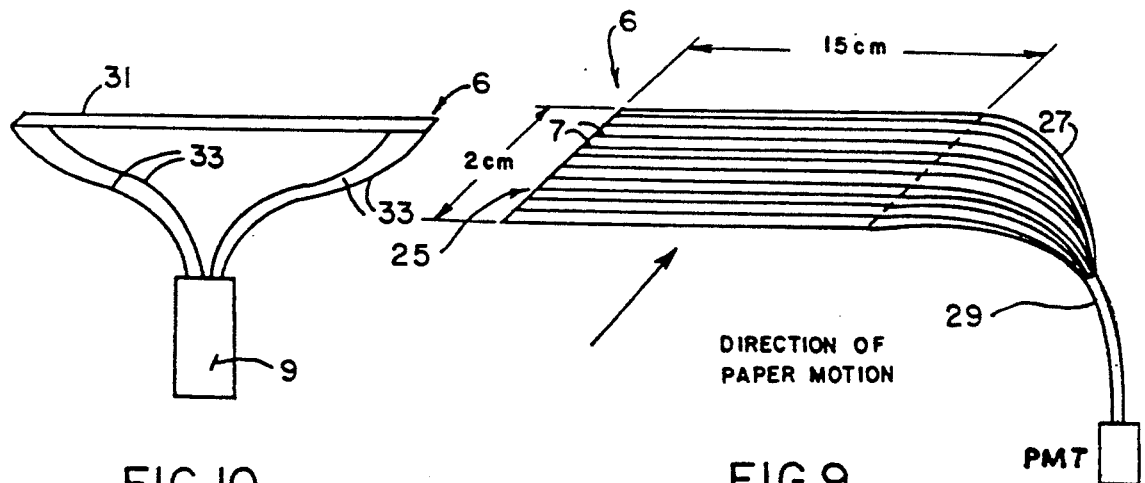
FIG. 9 is a schematic of a second embodiment of the detector array of FIG. 8.
FIG. 10 is a schematic of a third embodiment of a detector array for use with the basis weight detector.

FIG. 9 shows a second way to pipe the light to the photomultiplier tube. In this embodiment, the scintillating fibers are formatted into a single large non-scintillating fiber 29 which is then routed to the photomultiplier tube. For example a 3 cm wide ribbon of 1 mm square fibers, consisting of 30 fibers can be formatted into a 5×6 mm array with a diagonal of 7.8 mm. This output area can be connected to a circular or square non-scintillating fiber which is then routed to the photomultiplier tube 9. Because 100 KeV electrons penetrate through only about 150 $\mu$m of plastic, the fibers could be considerably smaller, e.g. 200 $\mu$m square, and still detect most of the light. This would correspond to 3 cm/0.02 cm=150 fibers which could be formatted into a square with a diagonal of about 2.5 mm. A 40 mm×40 mm, multi-anode (16×16 array) photomultiplier tube would work well in this arrangement since it could detect light from many fiber ribbons.

Figure 11:
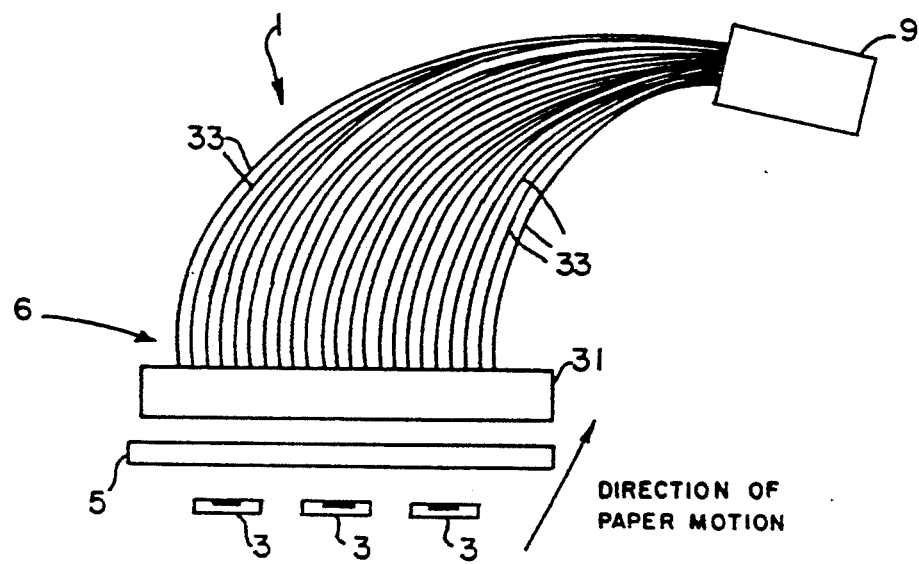
FIG. 11 is a fourth embodiment of a detector array for use with the basis weight detector.
Figure 12:
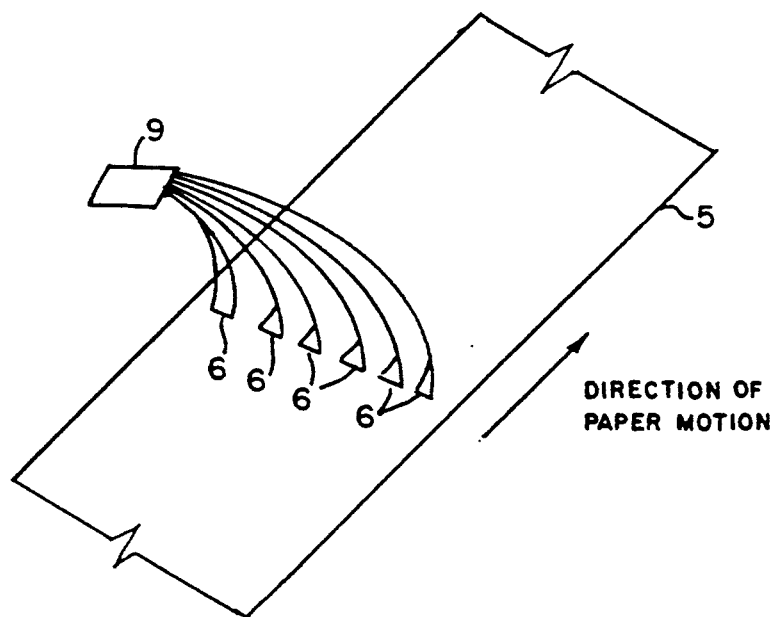
FIG. 12 is a perspective view of a basis weight detector apparatus having detector arrays exiting across the full width of a web of paper.

In another embodiment, FIGS. 10 and 11, array 6 is made of non-scintillating fibers tipped with a scintillating or phosphor screen 31. The fibers are coupled to screen 31 with an optically transmitting adhesive or epoxy such as an RTV silicon adhesive. In this embodiment the screen strip could be covered with 2 mm square non-scintillating fibers 33, for example. The strip could have a width of 15 cm. Thus the total output area for each group of fibers is 3.0 cm². A single photomultiplier tube (not a multi-anode tube) would be required for each 15 cm strip. The non-scintillating fibers 33 could alternatively each be capped with a scintillating element, rather than all the fibers being connected to a scintillating screen.

The screen is roughly six times more efficient than plastic scintillator. Therefore, making the same assumptions as in the above example, about eighteen photoelectrons per Beta decay electron enter the fibers. This greater efficiency allows the signal to be distinguished from background noise much more easily.

The solid angle subtended by the 2 mm strip is fifteen times less than the 3 cm width of the scintillating fiber. Therefore, a larger activity radiation source is required. However if, instead of using a single line of 2 mm fibers, a 3 cm×15 cm array of 2 mm fibers is used, more Beta particles can be detected using roughly the same source activity as for scintillating fibers. This embodiment, however, requires a larger single photomultiplier tube for each 15 cm width measurement.

It is essential to be able to calibrate the device 1 while it is in use to insure that measurements are not degraded because of water or dirt buildup on the sources or fiber arrays. Calibration can obviously be performed during machine down time. This, however, is expensive. It is preferable to calibrate the machine while it is operating to avoid any down time. Calibration while the machine is running can probably be best accomplished by having dual measurements for each source, detector, or module. The two measurements must agree with each other and with the calibration taken during the machine downtime. If the two measurements do not agree, then it is likely that water or dirt has collected between the source and fiber detector. When this happens, a cleaning mechanism must be activated to remove the contaminant. This cleaning mechanism could consist of, for example, a jet of air, a "wiper" to remove the contaminant, or perhaps some other mechanism. For example, an obtuse "oval" of detectors and sources could be periodically moved, i.e. much like a chain of a bicycle going around sprockets. As each detector gets off line from the edge of the paper, it is tested for calibration.

Figure 13:
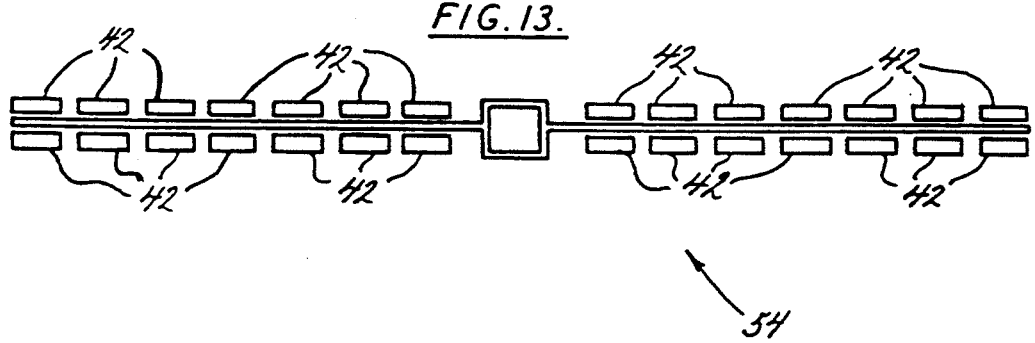
FIG. 13 is a top view of the basis weight detector of the present invention showing the arrangement of multiple detector arrays.
Figure 14:
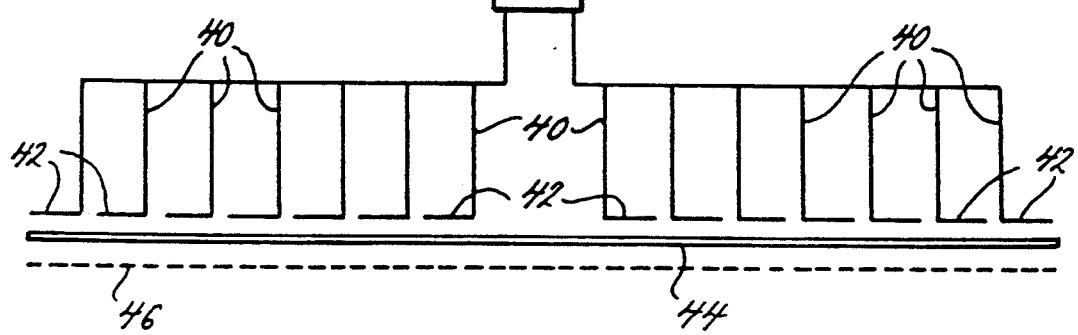
FIG. 14 is a side view of the embodiment shown in FIG. 13 wherein the multiple detector arrays blanket the moving web for detection of the thickness thereof across its width.
Figure 15:
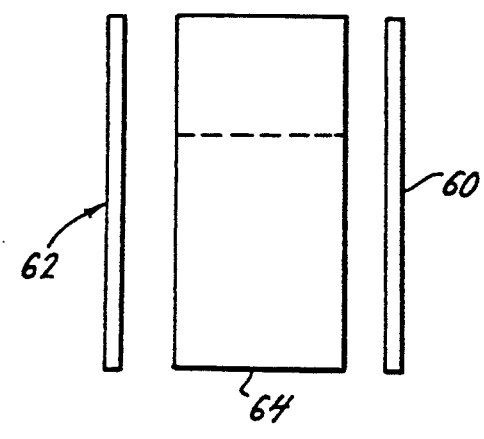
FIG. 15 is a side view of another embodiment of the present invention as used for detecting the fill level in a container.

A commercial embodiment of the present invention is further detailed in FIGS. 13 and 14. As shown therein, a plurality of detectors 40 have a bottom portion 42 extending substantially parallel to the traveling web 44 and are arranged in two banks (FIG. 13) to substantially cover the full width of the traveling web 44. Additionally, the detector ends 42 are arranged immediately above the radioactive source 46 which is arranged to extend transversely of the traveling web 44. The detector ends 42 may conveniently cover virtually all of the width of the web 44, although, for clarity, they have not been depicted as such in FIGS. 13 and 14.

As explained above, each of the detector ends 42 may be comprised of a plurality of contiguous scintillating fibers of approximately three centimeters in width which then extend upwardly to form the body of the detector 40 and be bundled conveniently to "light pipe" and thereby illuminate an anode of a multi-anode photomultiplier tube 48. A plurality of photomultiplier amplifiers 50 may be connected to the multi-anode photomultiplier 48 and the amplified signals input to computer 52 for further processing, recording, and control of the sheet forming process utilizing the on-line, real time, continuous width data provided by the width detection system 54 as shown in FIGS. 13 and 14.

As shown in previous embodiments, and as explained above, by turning the individual fibers comprising each detector end 42 sideways, the data may be physically integrated to provide an average reading which could be more reliable and sufficient, depending upon the particular application involved. However, this is not necessary and the fibers could be turned "head on" or aligned with the direction of movement for the traveling web 44, with just their ends facing radiation source 46. In other applications, this more precise detector arrangement could be utilized.

The detector sensitivity may be varied as the web forming process is varied. Factors such as the web speed, the radiation source strength and degree of collimation of output, and sheet material characteristics are variable to change the sensitivity of the detector. All of these factors need to be taken into account when arranging a particular width detector for use in a particular application.

Figure 16:
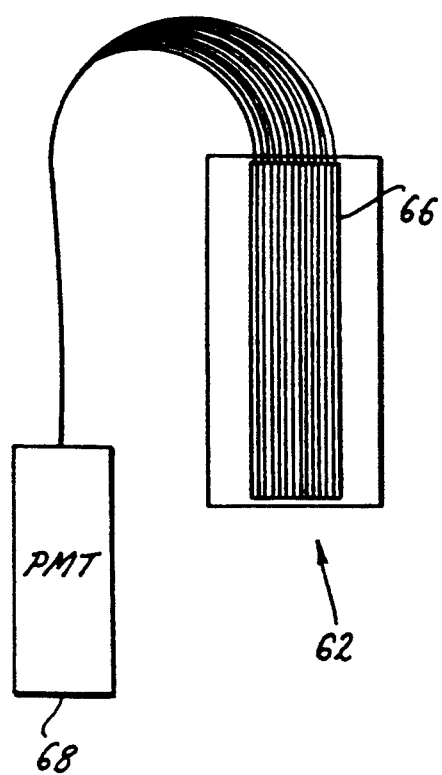
FIG. 16 is a side view of a first version of a receiver utilizing scintillating fibers arranged in a vertical orientation.

Another embodiment of the present invention is shown in FIGS. 15-18 and includes a linear radioactive source 60 which is arranged opposite from a receiver 62 in a spaced apart relationship to permit the passage therebetween of a plurality of containers 64 for containing fluid. The receiver 62 may be any one of several embodiments. One such example of a receiver embodiment 62 is shown in FIG. 16 and includes a generally vertical array of scintillating fibers 66 which are shown to extend substantially along the entire height of container 64 and which are then routed to an anode of a photomultiplier tube 68. The scintillating fibers 64 may extend for less than the full height of the container 64 and instead be concentrated at the upper portion thereof as most container 64 will have some amount of fluid reliably contained therein.

Figure 17:
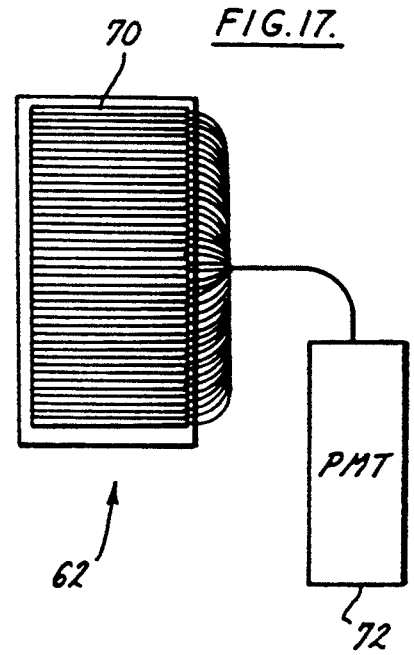
FIG. 17 is a view of a second version of the receiver with scintillating fibers arranged generally horizontally.

Still another embodiment of a receiver 62 is shown in FIG. 17 and includes a plurality of scintillating fibers 70 which are arranged generally horizontally to the container 64 and which are also gathered into a suitable array for light piping photons to the photomultiplier tube 72. As with the embodiment shown in FIG. 16, a reduced number of fibers could be arranged along the upper part of the receiver 62 to account for the fact that a certain amount of fluid may be reliably assumed to be contained within each container 64. Although a single anode photomultiplier tube 72 may be utilized and no differentiation made between radiation received at the upper or lower portion of the scintillating fiber array 70, in a variation thereof fibers may be grouped and fed to individual anodes of a multi-anode photomultiplier tube to thereby provide a more direct physical indication of the actual fill level in the container 64.

Figure 18:
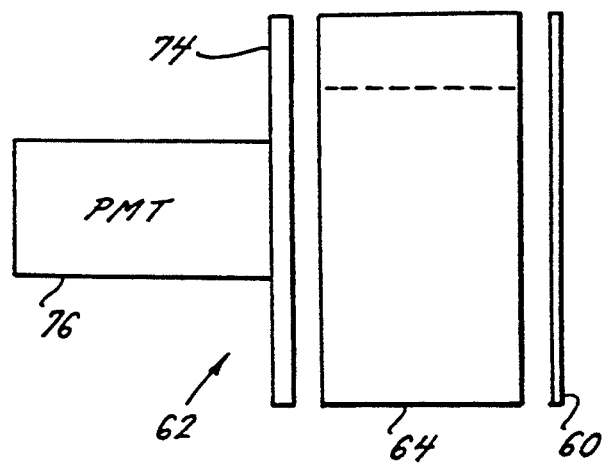
FIG. 18 is a side view of another arrangement of the embodiment of FIG. 15 except that the receiver comprises a plastic scintillator sheet coupled to a photomultiplier tube.

Still another embodiment is shown in FIG. 18 and includes the same linear radioactive source 60 but a different receiver 62 comprised of a plastic scintillator sheet 74 which is directly coupled to a single anode photomultiplier tube 76

In operation, the embodiment shown in FIGS. 15-18 is elegantly simple and direct. As a plurality of containers 64 are conveyed between the radioactive source and receiver, the radiation emitted from the source is absorbed by the fluid which is directly positioned between the source and the receiver. However, the portion of the container which does not have fluid fails to attenuate the radiation being emitted from the source, or at least attenuates the radiation to a lesser extent, such that a greater amount of radiation is received by the receiver to thereby indicate that that particular container is not completely filled. This mode of operation is experienced for those receivers which do not contain scintillating fibers grouped into arrays. In the embodiment shown in FIG. 17, individual groupings of scintillating fibers at varying levels produce stronger signals when the container position corresponding to the location of that grouping does not have fluid present thereat. Thusly, a more direct physical measurement is made and it is believed that the actual fill level can be measured more closely in that arrangement.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A detector for simultaneously measuring the thickness of a traveling web at multiple locations across its width comprising:
   a radiation source for emitting radiation which passes through said traveling web at each of said multiple locations; and
   a receiving means positioned at each of said multiple locations, said receiving means having means for receiving the radiation which passes through the web; said receiving means including means for converting said received radiation into a signal, said signals thereby being representative of the web thickness at said receiving means locations.

2. The detector of claim 1 wherein each of said receiving means is comprised of at least one scintillating fiber, the scintillator in said fiber further comprising said converting means.

3. The detector of claim 1 wherein each of said receiving means is comprised of a plurality of scintillating fibers, the scintillator in each of said fibers further comprising said converting means.

4. The detector of claim 3 wherein said fibers are arranged contiguously and transversely to the direction of travel of said web.

5. The detector of claim 4 wherein said conversion means further comprises a multi-anode photomultiplier tube, each of said receiving means having its fibers connected to a single anode of said multi-anode photomultiplier tube.

6. The detector of claim 5 wherein each of said receiving means has its fibers arranged along a portion of the width of the web, and adjacent receiving means have their fibers arranged substantially adjacent to each other to thereby cover substantially the entirety of the width of the web.

7. The detector of claim 6 wherein each of said receiving means has only a portion of its fibers arranged transversely to said traveling web.

8. The detector of claim 1 wherein each of said receiving means includes a scintillating means as its converting means, said converting means including at least one photomultiplier means, and a plurality of light pipes for communicating the output of said scintillating means to said photomultiplier means.

9. A detector for continuously measuring the thickness of a traveling web along substantially its entire width comprising:
   a radiation source extending along substantially the entirety of the web's width; and
   a receiving means extending along substantially the entirety of the web's width; said receiving means including means for converting the radiation which passes through the web and is received by the receiving means into a plurality of signals, each of said signals being representative of the instantaneous thickness of said web at a different transverse position of said web as it travels through said detector.

10. The detector of claim 9 wherein said receiving means comprises a plurality of receivers, said receivers being spaced transversely across the width of said web.

11. The detector of claim 10 wherein said conversion means comprises a multi-anode photomultiplier means, each of said receivers being connected to an anode of said multi-anode photomultiplier means.

12. The detector of claim 11 wherein each of said receivers comprises a plurality of scintillating fibers.

13. The detector of claim 12 wherein each of said plurality of scintillating fibers has a section thereof arranged contiguously and transversely to the path of said traveling web.

14. The detector of claim 9 wherein said receiving means includes a scintillating means as its converting means, said converting means including at least one photomultiplier means, and a plurality of light pipes for communicating the output of said scintillating means to said photomultiplier means.

15. A detector for continuously measuring the thickness of a traveling web at a plurality of positions spaced transversely across its width comprising:
a radiation source means positioned on one side of said web and having means for generating radiation through said web at least in said plurality of positions; and
a receiver means positioned on the side of said web opposite said radiation source means and having means for receiving radiation which traverses said web at said plurality of positions, said receiver means including means for converting the received radiation into a plurality of signals, said signals being representative of the instantaneously measured thickness of said web at said plurality of positions.

16. The detector of claim 15 wherein said conversion means further comprises a multi-anode photomultiplier means, said receiver means comprises a plurality of receivers, and wherein each of said receivers is connected to a separate anode of said multi-anode photomultiplier means.

17. The detector of claim 16 wherein each of said receivers has as its converting means scintillating means for converting said received radiation into light, and means for light piping said converted light to said anodes.

18. The detector of claim 17 wherein said scintillating means comprises a length of scintillating fiber, and said light piping means comprises optical fiber.

19. The detector of claim 18 wherein said length of scintillating fiber and optical fiber comprises a single length of scintillating fiber, and each receiver includes a plurality of said scintillating fibers arranged contiguously and transversely to the path of said traveling web.

20. A detector for continuously measuring the thickness of a traveling web at a plurality of locations along its width comprising:
a radiation source positioned on one side of said web and having means for generating radiation through said web at least in said plurality of locations;
a plurality of receiver means positioned on the side of said web opposite said radiation source; and
a multi-anode photomultiplier means, each of said receiver means consisting of a plurality of scintillating fibers integrally extending to an anode of said multi-anode photomultiplier means.

21. A detector for measuring the fill level of a fluid in each of a plurality of containers as said containers are conveyed past said detector, said detector comprising:
a radiation source for emitting radiation which passes through said container; and
a receiving means for receiving the radiation which passes through said container, said receiving means including means for converting said received radiation into a signal, said signal thereby being representative of the fill level of said container.

22. The detector of claim 21 wherein said receiving means further comprises a plurality of scintillating fibers, the scintillators in said fibers further comprising said converting means.

23. The detector of claim 22 wherein said plurality of fibers are arranged contiguously and substantially along at least that portion of the container having the greatest likelihood of being empty in the event of an under filled condition.

24. The detector of claim 23 wherein said fibers are arranged to substantially cover the entire height of the container.

25. The detector of claim 23 wherein said fibers are arranged substantially vertically and wherein said converting means further comprises a photomultiplier means, said fibers having their output connected to said photomultiplier means.

26. The detector of claim 23 wherein said fibers are arranged substantially horizontally and wherein said converting means further comprises a photomultiplier means, said fibers having their outputs connected to said photomultiplier means.

27. The detector of claim 26 wherein said fibers are grouped into a plurality of separate groups, each of said groups thereby corresponding to a different level of fill of said container, and wherein said photomultiplier means has a plurality of separate inputs, each of said groups being connected to one of said inputs to thereby provide an output representative of the relative fill level of said container.

28. The detector of claim 21 wherein said converting means comprises a scintillating means and a photomultiplier means directly connected to said scintillating means.

29. A detector for continuously measuring the areal density of a material at a plurality of positions spaced transversely across said material's width comprising:
a radiation source means positioned on one side of said material and having means for generating radiation through said material at least in said plurality of positions; and
a receiver means positioned on the side of said material opposite said radiation source means and having means for receiving radiation which traverses said material at said plurality of positions, said receiver means including means for converting the received radiation into a plurality of signals, said signals being representative of the instantaneously measured areal density of said material at said plurality of positions.

30. A detector for continuously measuring the areal density of a material along a substantial portion of a length dimension thereof, said detector comprising a radiation source extending along said substantial length portion of said material and a receiver means extending along said substantial length portion of said material, said receiving means including means for converting the radiation which passes through the material and is received by the receiving means into a plurality of signals, each of said signals being representative of the instantaneous areal density of said material at a different position along said length dimension of said material as it travels through said detector.

* * * * *